United States Patent [19]

Dobo et al.

[11] 4,267,138

[45] May 12, 1981

[54] COATING ENSURING A CONTROLLED RELEASE OF ACTIVE INGREDIENTS OF BIOLOGICALLY ACTIVE COMPOSITIONS, PARTICULARLY PHARMACEUTICAL COMPOSITIONS AND A PROCESS FOR PREPARATION OF BIOLOGICALLY ACTIVE COMPOSITIONS ENSURING CONTROLLED RELEASE OF ACTIVE INGREDIENTS

[75] Inventors: Janos Dobo; Erzsebet Takacs; Gyozo Hortobagyi; Marianne Skvorecz nee Hajnoczy; Ilona Kolbe; Katalin Hoffmann nee Vas, all of Budapest, Hungary

[73] Assignee: Richter Gedeon Vegyeszeti Gyar Rt., Budapest, Hungary

[21] Appl. No.: 834,492

[22] Filed: Sep. 19, 1977

[30] Foreign Application Priority Data

Sep. 17, 1976 [HU] Hungary .................................. 596

[51] Int. Cl.³ .............................................. A61J 3/10
[52] U.S. Cl. .................................. 264/117; 264/109; 424/19; 424/33; 424/81; 427/3
[58] Field of Search ................ 427/3; 424/19, 33, 22, 424/81; 264/117, 109

[56] References Cited

U.S. PATENT DOCUMENTS

| Re. 27,107 | 3/1971 | Levesque | 424/22 |
|---|---|---|---|
| 3,148,124 | 9/1964 | Gaunt | 424/22 |
| 3,655,129 | 4/1972 | Seiner | 424/22 |
| 3,773,919 | 11/1973 | Boswell | 424/22 |
| 3,923,939 | 12/1975 | Baker | 424/22 |

*Primary Examiner*—Sam Silverberg
*Attorney, Agent, or Firm*—Karl F. Ross

[57] ABSTRACT

A coating ensuring the controlled release of a biological active ingredient, which can be incorporated in the coating or is surrounded thereby, consists of a varnish-forming polymer selected from the group which consists of cellulose triacetate containing polyethylene glycol as an emollient and vinyl chloride-vinyl acetate copolymer with glycerol as an emollient, and an aqueous phase dispersed in the polymer and consisting of particles of a diameter up to 20 microns, the aqueous phase making up 2% to 30% of the volume of the coating. The active ingredient is preferably a pharmaceutical agent affecting the circulatory system or a psychotropic agent.

8 Claims, 2 Drawing Figures

COATING ENSURING A CONTROLLED RELEASE OF ACTIVE INGREDIENTS OF BIOLOGICALLY ACTIVE COMPOSITIONS, PARTICULARLY PHARMACEUTICAL COMPOSITIONS AND A PROCESS FOR PREPARATION OF BIOLOGICALLY ACTIVE COMPOSITIONS ENSURING CONTROLLED RELEASE OF ACTIVE INGREDIENTS

FIELD OF THE INVENTION

The present invention relates to coatings ensuring controlled release of active ingredients of biologically active compositions, particularly pharmaceutically active compositions, to biologically active compositions with controlled release of active ingredients and to a process for the preparation thereof.

BACKGROUND OF THE INVENTION

In several fields and especially in the field of pharmaceutical compositions there is a need for compositions having controlled release of active ingredients. In the case of pharmaceutical compositions such units are of special importance when a long lasting steady blood level of the active ingredient administered to the body is required to obtain a suitable therapeutic effect. These active ingredients are e.g. analgesics, pharmaceutical compositions acting upon the circulatory and vascular system, sedatives, and antihistamines. The release of the active ingredient is ensured for a longer time by administering additional doses of the composition containing the active ingredient at certain intervals, due to which, however, a fluctuation of the blood level takes place. This disadvantage should be eliminated by compositions for controlled release of active ingredients.

Several methods are known for the preparation of compositions for controlled release of active ingredients. In some methods the active ingredient is admixed with inert substances such as waxes or polymers and the mixture is compressed into tablets. The preparation of such so called frame tablets is described in the German patent publication No. 1 258 458. A relatively large amount of inert frame material is required to prepare such tablets and thus voluminous and not easily deglutible tablets are obtained. In many cases a very high temperature is required to compress the tablets and the active ingredient may be damaged by such temperatures.

The preparation of compositions of controlled release of active ingredients has been improved by introducing varnishes, which ensure the delayed release of the active ingredients by diffusion. Various homo and copolymers are used to prepare varnishes of suitable diffusion rates (see e.g. British patent specification No. 833 458 and German Pat. Nos. 1 279 896 and 1 949 894). The required mechanical properties and the suitable tenacity of the varnish layer are obtained by emollients and other additives. The addition of emollients is especially important if the basic material of the polymer forming the varnish is a solid vitreous substance at room temperature, such as polymers of the acrylate and metacrylate type. On storage of the tablets, however, the emollients and the various additives easily diffuse and migrate from the thin varnish film layers. Thus the varnish materials of the tablets become brittle on storing, and the permeability properties change. To avoid this in some cases a relatively larger amount of emollient is employed. The employment of a large amount of emollients is however disadvantageous in other respects. An important part of the emollients consists of an ester type or polyalcohol type small molecule and as such they are a good medium for the growth of microorganisms. That is why the use of emollient-containing plastics as packing material in the food industry is limited. Similarly the use of such substances in a protecting covering of pharmaceutical compositions should be avoided. It is difficult to control the release of active ingredients by varnishes if the permeability of the varnish has to be adjusted for active ingredient molecules of definite size and diffusion. It is rather complicated to prepare a varnish forming polymer for each active ingredient molecule; thus the desired varnish is usually prepared by mixing together a varnish of good permeability and a varnish of low permeability in a suitable ratio.

It is known however, that various polymers even copolymers of identical composition but of different monomer ratio, are generally not well miscible. After the removal of the solvent such polymer mixtures often separate and a product of poor quality is obtained.

Similarly problems arise if plant protecting agents, insecticides, pheromones or other biologically active ingredients with delayed action need to be prepared.

DESCRIPTION OF THE INVENTION

This invention is directed to the elaboration of a coating by means of which compositions of controlled release of active ingredients can be prepared without the disadvantages mentioned above.

The invention is based upon the surprising fact, that a coating for compositions of controlled release of active ingredients can be prepared if the active ingredient or the composition containing the active ingredient is coated with a polymer varnish coating containing a finely dispersed aqueous layer. The coating thus prepared has the advantage that the dispersed aqueous layer makes the coating more permeable.

The permeability properties of the varnish can be further modified if one or several additives, such as emollients, related to the polymer, wetting agents, buffers or hygroscopic substances are added to the aqueous layer.

The coating of the invention is advantageous as the permeability of the coating can be varied within a wide ranges by the suitable choice of the solvent, the solvent system or the additives contained in the aqueous layer. A further advantage of the process is the fact that by varying the solvent or the solvent system it is not necessary to store and mix two basic solutions to obtain a varnish of suitable permeability, but the desired coating can be obtained from one single stock solution in a wide transmission range.

BRIEF DESCRIPTION OF THE DRAWING

The accompanying drawing consists of FIGS. 1 and 2 which are graphs illustrating the invention. In order to characterize the permeability properties of the coating according to the invention, the permeability of p-nitrophenol as a model substance through a film formed of the coating of the invention is illustrated in FIG. 1 compared with film layers formed of the commercially available Eudragit retard varnishes of small or large permeability (i.e. RS 12.5 and RL 12, respectively). The measurements were carried out at 37° C., in a buffer of 0.1 molar sodium acetate at pH=4 under suitable stirring. The rate of the transmission through the foil was determined on a spectrophotometer at 405 nm. The results refer to identical thickness of the foil. The transmission through a cellulose triacetate foil prepared by the same method but not containing any dispersed layer is so slow that it cannot be measured by the above method.

The curves in FIG. 1 are as follows:

Figure 1:
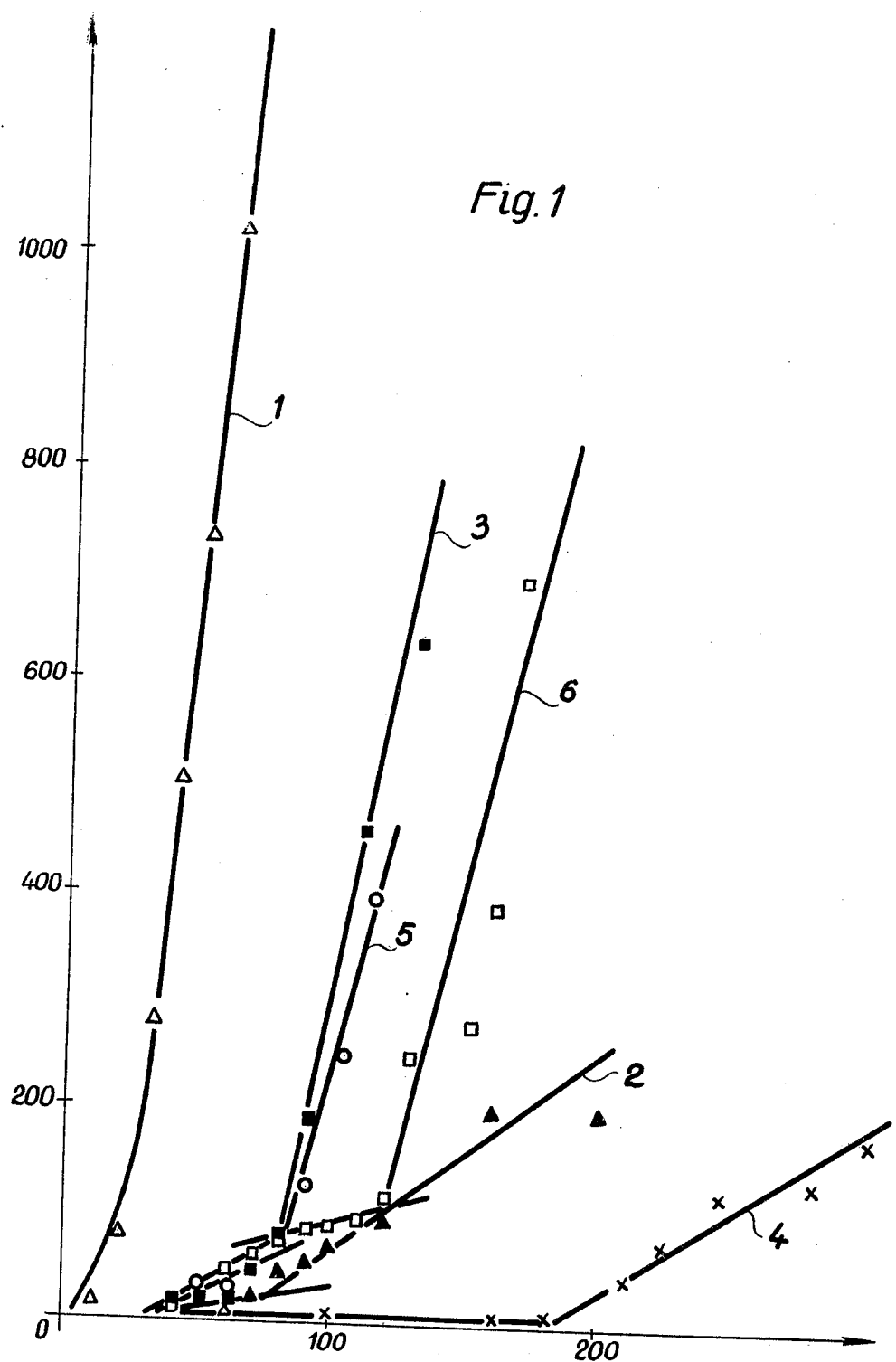

Curve 1: The transmission curve of a cellulose triacetate foil containing 50% by weight dispersed layer, where the dispersed layer consists of 8 parts by weight of water, 2 parts by weight of polyethyleneglycol (molecular weight: 6000). The foil was prepared from a 10% solution, the solvent consisted of 9 parts by weight of dichloromethane and 1 part by weight of toluene.

Curve 2: The transmission curve of the same foil with the exception that the solvent consists of dichloromethane without toluene.

Curve 3: The transmission curve of the same foil with the exception, that the dispersed layer consists of 3 parts by weight of glycerol and 7 parts by weight of water.

Curve 4: The transmission curve of the same foil with the exception that the solvent is pure dichloromethane and the dispersed layer consists of 3 parts by weight of glycerol and 7 parts by weight of water.

Curve 5: Transmission curve of a foil prepared of the varnish solution containing 2% glycerol Eudragit RL 12.5 (prepared by Röhm und Haas Pharma GmBH (Darmstadt).

Curve 6: Transmission curve of a foil prepared of the varnish solution containing 2% glycerol Eudragit RS 12.5 (prepared by Röhm und Haas Pharma GmBH (Darmstadt).

The invention also is a polymer based coating composition material ensuring controlled release of the active ingredients of biologically active compositions, particularly pharmaceutical compositions containing a varnish-forming polymer dissolved in a water inmiscible organic solvent or solvent mixture and being insoluble in water and in the case of pharmaceuticals substantially insoluble in gastrointestinal juices and further containing an aqueous layer dispersed in the polymer and consisting of particles of a diameter up to 20μ, preferably 1 to 5μ, wherein the aqueous layer makes out 2 to 30%, preferably 3 to 8% of the total volume, and the particles of the aqueous layer contain one or several additives, such as an emollient with respect to the polymer, a buffer, a wetting agent, a hygroscopic material and optionally a part of the active ingredient as well.

As polymers, preferably cellulose esters, particularly cellulose triacetate, polyvinyl chloride and vinyl chloride copolymers are employed in the coating but other varnish forming polymers are also suitable.

Cellulose triacetate is particularly preferred as it remains undigested (Encyclopaedia of Polymer Science and Technology, Volume 3, page 448, 1965) and if a small part is metabolized then acetic acid and cellulose, that is such which are substances present in the body in a large amount, are formed.

As an emollient the dispersed layer contains preferably glycerol, polyethyleneglycol, dioctylsulfate or phosphoric acid esters. The molecular weight of the emollient is preferably greater than that of the active ingredient.

As buffers in the dispersed layer preferably acidic and basic buffers are used, such as buffers including sodium salicylate, sodium citrate and ion exchanging substances.

As a wetting agent the aqueous layer contains preferably sodium lauryl sulfate, sodium dioctyl-sulfo-succinate, polyoxyethylene-sorbitan-monofatty acid esters.

In preparing pharmaceutically active substances, the additives must be pharmaceutically acceptable.

The advantage of the process of the present invention is in storing the additives in the aqueous disperse layer in a protected state i.e. free of any bacterial infections. Even additives capable of promoting bacterial growth may be employed without any danger by the aid of the present invention since the main part of these substances is contained in the aqueous layer in dissolved or a finely dispersed state. Thus these substances only reach the organic polymer medium of the varnish layer at the rate of their evaporation, release or transmission.

The coating of the present invention is prepared by dissolving the polymer in a suitable, water immiscible organic solvent or a solvent mixture and water in a ratio of about 2 to 30%, preferably 3 to 8% of the total volume of the solution is dispersed in the solution, and the water may, if desired, contain one or several additives, and optionally an active ingredient as well. The dispersion is carried out in a colloid mill. According to another method the amount of the water necessary to form the aqueous layer is subdivided to several parts and the various additives are dissolved in these parts, whereafter these parts are dispersed separately in the polymer dissolved in an organic solvent. Following the stabilization of the varnish layer several dispersions will be present in the varnish layer substantially without being mixed and the interaction of each dispersion will be dependent upon the diffusion processes in the varnish layer. This process makes it possible to obtain an aqueous layer wherein the additives are present in the form of discrete immiscible particles as the particles of the aqueous dispersion do not mix and do not change after the formation thereof.

A further aspect of the present invention are biologically active products, particularly pharmaceutical compositions and a process for the preparation thereof. The compositions according to the invention containing the biologically active ingredient, particularly the pharmaceutically active substance or granules containing such an active ingredient in the form of tablets, granules, pellets are coated by a coating which contains a varnish forming polymer insoluble in water and in the case of pharmaceutically active substances substantially insoluble in gastrointestinal juices and a dispersed aqueous layer consisting of particles of a diameter of up to 20μ, preferably 1 to 5μ wherein the aqueous layer amounts to 2 to 30%, preferably 3 to 8% of the total volume. The particles of the aqueous layer contain optionally one or several additives, such as an emollient related to the polymer, a wetting agent, a buffer and a hygroscopic substance and they can optionally contain a part of the active ingredient too, and the composition may optionally contain a layer including a further active ingredient. A preferable group for the compositions of controlled release of active ingredients contains the active ingredient only in the particles of the aqueous layer.

The compositions thus obtained release the active ingredient through the coating in a regulated way. If for example a tablet prepared from a pharmaceutically active compound is coated as described above the gastric juices penetrate into the gastro-intestinal tract to the inner side of the composition by passing through the film coating and dissolve the active ingredient.

The saturated solution of the active ingredient diffuses back through the coating into the surroundings according to the concentration gradient against the surroundings. According to another method the initial dose, i.e. the dose ensuring the optimal blood level for obtaining a therapeutic effect is introduced to the aqueous layer of the coating, while the maintainance dose is to be found under the coating. This composition is of advantage if the initial dose is low. In the case of a higher initial dose the starting dose is applied on the coating in an outer dragee covering after coating the maintainance dose with the coating according to the invention.

According to a preferred embodiment of the present invention the polymer is dissolved in a suitable, water immiscible organic solvent or a solvent mixture, the aqueous layer is dispersed in the solution, which can optionally contain one or several additives and optionally also a part of the ingredient, whereafter the obtained coating dispersion is applied on the surface of the active ingredient or granules containing the active substance and the organic solvent is evaporated and thus the coating is stabilized and, if desired, a further layer containing another active ingredient is applied on the coating by known techniques.

By employing the coating of the invention a frame tablet of controlled release of active ingredients may also be prepared. In this case the granulate containing the active ingredient is, after coating the granulate with a coating according to the invention and after adding the usual additives, compressed into tablets.

Thus the coating on the surface of granules deformed during the pressing is partially torn on pressure and a bond is formed at the coating-interface. Thus a frame structure is formed from the coating and the active ingredient releases slowly from the cavities of the frame structure.

The invention is further illustrated by the following Examples:

EXAMPLE 1

100 g. of cellulose triacetate are dissolved in 1200 ml. of dichloromethane. To this solution 20 g. of polyethyleneglycol of an average molecular weight of 6000 in 80 ml. of water is added, whereafter the aqueous solution is dispersed at 20° C. in a colloid mill to an emulsified phase of particles of a diameter of 1 to 5 micron. The thus prepared varnish solution is used as a coating and in an air current at 40° C. the steady release of active ingredients of a molecular weight of 150 to 400 is ensured.

EXAMPLE 2

100 g. of vinyl chloride vinyl acetate copolymer are dissolved in 1200 ml. of dichloromethane, wherein the ratio of the monomers is 8:2. The mixture of 80 ml. of water and 20 ml. of glycerol is added to the solution and the aqueous solution is dispersed at 20° C. in a colloid mill to an emulsified phase of particles of a diameter of 1 to 5μ. The thus prepared varnish solution is used as a coating and by stabilizing it at 40° C. in air current the steady release of active ingredients of a molecular weight of 150 to 400 is ensured.

EXAMPLE 3

100 g. of cellulose triacetate are dissolved in 1080 ml. of dichloromethane and 120 ml. of toluene and the mixture is further treated as described in Example 1. The thus prepared varnish solution is suitable for coating active ingredients of a molecular weight of 300 to 600.

EXAMPLE 4

1000 g. of bamethan sulfate and 1360 g. of lactose are homogenized. The homogeneous dust mixture is steadily wetted with 50 g. of polyvinylpyrrolidone in 450 g. of water. The wet mass is granulated in an oscillating granulator equipped with a 2 mm. mesh screen and dried on a tray drier or a fluidizer cabinet drier. The dry mass is regranulated in a granulator provided with a 0.8-1.0 mm. mesh screen. 20 g. of magnesium stearate and 70 g. of talc is added. From the homogeneous mixture convex tablets weighing 250 g. and in diameter of 9 mm. are compressed by the means of a suitable tabletting machine.

The tablets are coated in a dragee pan with the whole amount of the coating substance obtained in Example 1. The coating dispersion is preferably applied on the tablets with a pneumatic or hydraulic spraying gun. The solvent is evaporated by blowing warm air into the system.

The bamethan sulfate is released in the gastro-intestinal tract over several hours from the coated tablet.

EXAMPLE 5

10 g. of reserpine and 1880 g. of lactose is granulated with a solution of 40 g. of polyvinylpyrrolidone in 360 g. of water as described in Example 3. 10 g. of magnesium stearate and 60 g. of talc is added to the granulate and it is pressed to obtain convex tablets weighing 200 mg. and in diameter of 8 mm.

The tablets are coated as described in Example 4 by employing a coating prepared as described below: 1200 g. of cellulose triacetate are dissolved in 1200 g. of dichloromethane, 1 g. of tartaric acid, 1 g. of ascorbic acid and 10 g. of polyethylenglycol of an average molecular weight of 6000 and 1 g. of reserpine are dissolved in 87 ml. of water. The aqueous solution is dispersed in a solution containing dichloromethane and the tablets are coated with the emulsion.

The reserpine is first absorbed from the coating of the tablet in the gastrointestinal tract and thus the blood level necessary to the therapeutical effect is formed, and the maintainance dose is released for several hours from the tablet nucleus through the cellulose triacetate.

EXAMPLE 6

200 g. isosorbide dinitrate and 40 g. of stearine are dissolved in 800 g. of chloroform. The chloroform solution is applied on 2150 g. of lactose. After evaporating the chloroform the mixture is granulated with the solution of 50 g. of polyvinylpyrrolidone in 450 g. of water as described in Example 4. 60 g. of talc are added to the mixture and convex tablets weighing 250 mg. and in diameter of 9 mm. are pressed.

The tablets are coated with a dispersion of cellulose triacetate according to Example 1 as described in Example 4.

The tablets coated with a cellulose triacetate film are coated according to the rules of pearl-coating with the suspension described below applied on each layer.

848 g. of succrose and then 6 g. of polyvinyl-pyrrolidone are dissolved in 438 g. of hot water. 4 g. of colloidal silicic acid (Aerosil), 64 g. of talc and 640 g. of secondary calcium phosphate are mixed to the solution. The suspension is homogenized in a colloid mill.

The conglobated granules are coated with a suspension of the following composition: 637.5 g. of succrose, 4.5 g. of polyvinylpyrrolidone and 100 g. of isosorbide dinitrate are dissolved in 328.5 g. of water. 3 g. of colloidal silicic acid (Aerosil), 48 g. of talc and 380 g. of secondary calcium phosphate are added to the solution.

The coated and dried granules are polished by usual methods.

After the dragées prepared as described above get into the gastro-intestinal tract the initial dose is first released from the outer coating to ensure the blood level necessary to the therapeutical effect. The maintainance dose is extracted from the dragée nucleus in several hours through the cellulose triacetate film.

EXAMPLE 7

On 6 kg. of pellets of a particle size of 0.6–0.8 mm. a suspension prepared as described below is applied in a fluidizer varnish dragée pan: 50 g. of carboxy-methyl-cellulose soduim and 250 g. of polyvinylpyrrolidone are dissolved in 3022 g. of water. 3 g. of sodium lauryl sulfate are dissolved in 1000 g. of water. 25 g. of colloidal silicic acid (Aerosil), 150 g. of talc and 100 g. of apovincaminic acid ethyl ester are added to the sodium lauryl sulfate solution. The suspension is homogenized in a colloid mill and is added to an aqueous solution of carboxy-methyl-cellulose sodium and polyvinylpyrrolidone.

4 kg. of the microdragée mass of apovincaminic acid ethyl ester prepared as described above is coated in a fluidizer varnish dragée pan with a cellulose triacetate dispersion described in Example 1.

A homogeneous mixture of uncoated apovincaminic acid ethyl ester microdragees and apovincaminic acid ethyl ester microdragées coated with a cellulose triacetate film of a ratio 1:2 is filled into hard gelatine capaulwa so that each capsule contains 200 mg. of micrdragée.

The capsule is perforated upon getting to the gastro-intestinal tract by the effect of gastric juices and the micro-dragées are mixed with the content of the stomach. The apovincaminic acid ethyl ester is digerated from the uncoated granules in an amount which is necessary to ensure the blood level needed for the therapeutic effect and the maintainance dose is released from the inner side of the microdragees coated with the cellulose triacetate film during several hours by diffusing through the film.

EXAMPLE 8

Tablets containing 100 mg. of bamethan sulfate are prepared as described in Example 4 and the tablets are coated with a coating according to Example 3 by the fluidization technique described in Example 7. The test results of the release of active ingredients of the tablets thus obtained are given below.

The extraction of the bamethane sulfate content of the tablets was tested in an eluting medium of 37° C. At the beginning of the test as eluting substance artificial gastric juice was used (pH=1.3) and in every 60 minutes the half of the solution was replaced by artificial intestinal juice (pH=7.3); the bamethane sulfate administered to the solution was determined in a sample simultaneously by spectrophotometric method.

The pH of the eluting medium was successively increased (so called half-change method, Münzel, K. : Arch. Pharm. 293,766(1960)).

Figure 2:
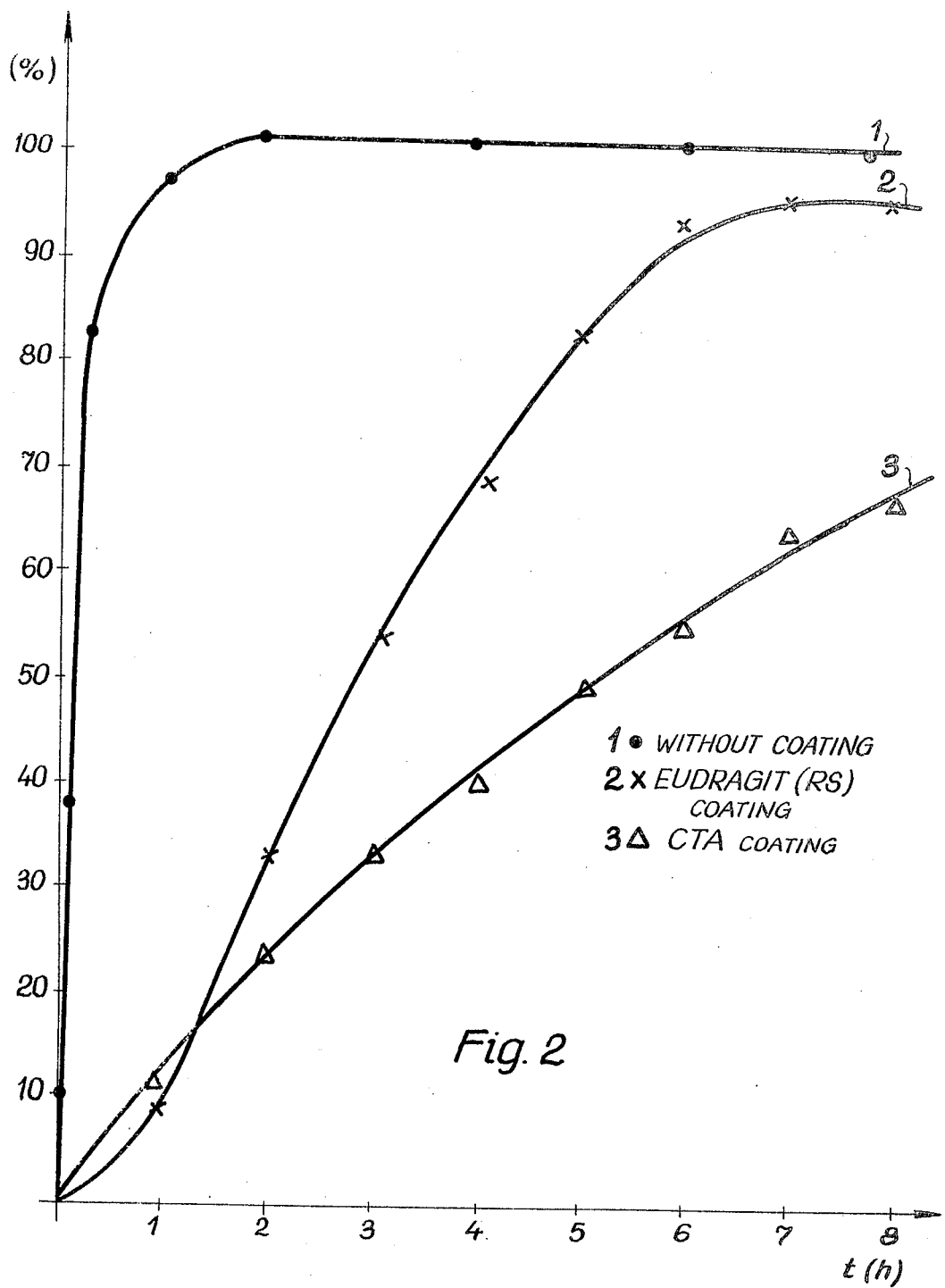

In FIG. 2 the percentage value of the active ingredient extracted from the composition is plotted against time.

Curve 1. shows the release of the active ingredient of the uncoated tablet.

Curve 2. shows the release of the active ingredient of tablets coated with Eudragit RS varnish.

Curve 3. shows the release of the active ingredient from tablets coated with the coating of the invention.

The curve shows, that the coating of the invention ensures a steady (kinetical O. order rate) release of active ingredients.

What we claim is:

1. A process for preparing a pharmaceutical for gastrointestinal release, comprising the steps of:
   (a) forming a water-in-oil emulsion from a solution of a varnish-forming polymer substantially unaffected by exposure to gastrointestinal juices in a water-immiscible solvent and an aqueous phase dispersed in the organic phase in particles not more than 20 microns in diameter, said aqueous phase constituting 2 to 30% of the total volume and containing at least one substance selected from the group which consists of a plasticizer, a wetting agent, a buffer and a hygroscopic substance;
   (b) coating granules of a pharmaceutical suitable for oral administration with the emulsion formed during step a) and evaporating the solvent to form a coating which substantially retains the aqueous phase of the emulsion dispersed throughout the varnish-forming polymer; and
   (c) agglomerating the granules coated during step b) into a pharmaceutical dosage unit.

2. The process defined in claim 1 further comprising the step of compressing the coated granules agglomerated during step (c) into tablets.

3. The process defined in claim 1 wherein the pharmaceutical is an agent acting upon the circulatory system.

4. The process defined in claim 3 wherein the agent acting upon the circulatory system is apovincaminic acid ethyl ester.

5. The process defined in claim 3 wherein the agent acting upon the circulatory system is bamethane sulfate.

6. The process defined in claim 3 wherein the agent acting upon the circulatory system is isosorbide dinitrate.

7. The process defined in claim 1 wherein the pharmaceutical is a psychotropically active substance.

8. The process defined in claim 7 wherein the psychotropically active substance is reserpine.

* * * * *